United States Patent [19]

Kemp et al.

[11] Patent Number: 5,106,949
[45] Date of Patent: Apr. 21, 1992

[54] COLLAGEN COMPOSITIONS AND METHODS FOR PREPARATION THEREOF

[75] Inventors: Paul D. Kemp, Cambridge; Lisa Falco, Medford; Kathleen Regan; Eugene Bell, both of Boston, all of Mass.

[73] Assignee: Organogenesis, Inc., Cambridge, Mass.

[21] Appl. No.: 407,465

[22] Filed: Sep. 15, 1989

[51] Int. Cl.⁵ .................... A61K 35/32; A61K 37/12; C07K 3/02; C07K 15/20
[52] U.S. Cl. ................................ 530/356; 424/572; 514/801
[58] Field of Search ...................... 530/356; 424/572; 514/801

[56] References Cited

U.S. PATENT DOCUMENTS

| | | |
|---|---|---|
| 2,598,608 | 6/1946 | Salo et al. . |
| 2,631,942 | 3/1953 | Highberger . |
| 2,920,000 | 1/1960 | Hochstadt et al. . |
| 4,404,033 | 9/1983 | Steffan . |
| 4,485,096 | 11/1984 | Bell . |
| 4,485,097 | 11/1984 | Bell . |
| 4,539,716 | 9/1985 | Bell . |
| 4,546,500 | 10/1985 | Bell . |
| 4,604,346 | 9/1987 | Bell et al. . |
| 4,835,102 | 5/1989 | Bell et al. . |
| 4,837,379 | 6/1989 | Weinberg . |

FOREIGN PATENT DOCUMENTS 285471 10/1988 European Pat. Off. .
285474 10/1988 European Pat. Off. .

OTHER PUBLICATIONS

Negroiu et al. CA vol. 113, 233700v p. 116, Jan. 30, 1989.

Primary Examiner—Howard E. Schain
Assistant Examiner—Choon P. Koh
Attorney, Agent, or Firm—David G. Conlin; Linda M. Buckley

[57] ABSTRACT

This invention relates to collagen compositions and methods of preparing such compositions. This invention also relates to a novel source of collagen, the common digital extensor tendon.

18 Claims, 1 Drawing Sheet

COLLAGEN COMPOSITIONS AND METHODS FOR PREPARATION THEREOF

BACKGROUND OF THE INVENTION

This invention pertains to collagen compositions and methods of preparing such compositions.

Collagen is usually found as the principal protein component of the extra-cellular matrix. In mammals, collagen sometimes constitutes as much as 60% of the total body protein. It comprises most of the organic matter of skin, tendons, bones and teeth, and occurs as fibrous inclusions in most other body structures. Collagen is a relatively weak immunogen, due in part to masking of potential antigenic determinants by the helical structure. This helical structure also makes collagen resistant to proteolysis. Collagen is a natural substance for cell adhesion and the major tensile load-bearing component of the musculo-skeletal system. Because of the foregoing properties, collagen has application in the manufacture of implantable prostheses, and in the preparation of living tissue equivalents.

Collagen is an essential component of living tissue equivalents which are prepared from a hydrated collagen lattice contracted by a contractile agent, such as fibroblast cells, smooth muscle cells or blood platelets. Such tissue equivalents are disclosed in U.S. Pat. Nos. 4,485,096; 4,485,097; 4,539,716; 4,546,500; 4,604,346; 4,835,102; and 4,837,379, all of which are incorporated herein by reference (hereinafter collectively referred to as "the Patents"). These tissue equivalents include, but are not limited to, equivalents of epithelial tissue and connective tissue such as skin, cartilage, bone, blood vessels, and comprise living cells and extracellular matrix molecules, principally collagen, and may optionally be provided with components not typically found in normal tissue. Such tissue equivalents have a broad range of applications including applications in research and development, tissue and organ replacement and testing.

Collagen compositions are typically prepared from skin and tendons by procedures involving acid or enzyme extraction. Enzyme extraction is preferable in many instances because this methodology produces increased yields and higher purity collagen. However, enzyme extraction suffers the disadvantage of producing partically degraded collagen, i.e., the extraction enzymes cleave the collagen molecule at the terminal non-helical regions which contain the inter-collagenous cross-linkages.

It has been found that collagen extracted by use of the enzyme pepsin, a frequently used enzyme for the production of enzyme extracted collagen, produces living tissue equivalents which are undesirably weak for certain applications, e.g., those which involve substantial mechanical handling of the tissue equivalent. Thus, improved collagen compositions and methods of preparing such compositions are being sought.

SUMMARY OF THE INVENTION

The present invention provides methods of preparing collagen compositions from tendons. Many methods of obtaining acid extractable collagen are known in the art. However, the methods of the present invention offer advantages over known methods both in terms of yield of acid extractable collagen and quality of living tissue equivalents produced by use of such collagen.

A preferred method for preparing collagen from tendon in accordance with the present invention comprises the steps:

(a) washing finely divided tendon from which the sheath has been removed in phosphate buffered saline at a pH of about 6.5 to 8.5;

(b) extracting collagen from the tendon obtained in step (a) with a weak acid and gentle mechanical action;

(c) precipitating the acid-extracted collagen obtained in step (b); and (d) recovering the precipitated collagen. A preferred agent for precipitating the extracted collagen is sodium chloride at a concentration of from about 0.6 to 1.8M. In some embodiments of the present invention steps (c) and (d) are accomplished by simultaneous precipitation and aeration, followed by pressure filtration of the precipitated collagen.

The methods of the present invention typically yield collagen at greater than about 4% of the wet weight of the finely divided tendon. Phosphate buffered saline comprising 0.05 M sodium chloride: 2.2 mM sodium phosphate buffer at a ratio of about 1:3 to 1:1 is a preferred saline for use in the present invention. Preferred acids include acetic and citric and formic acids.

The present invention also provides collagen isolated from a novel source, i.e., the calf common digital extensor tendon. Calf is a preferred source of such tendon.

DETAILED DESCRIPTION OF THE INVENTION

Figure 1:
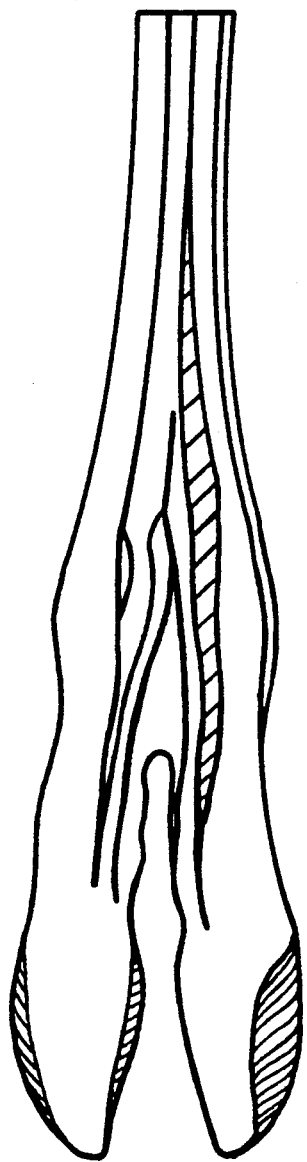
FIG. 1 is an illustration of a calf hoof showing the location of the common digital extensor tendon.

The present invention provides collagen isolated from a novel source, i.e., the calf common digital extensor tendon. This tendon contains an unexpectedly high amount of acid extractable collagen.

Collagen may be extracted from a variety of tissues but the two most common sources are skin and tendon. Tendons which may be used in the practice of the present invention include, for example, bovine tendon and rat tail tendon. Bovine tendons include cow tail tendon, cow Achilles tendon, calf Achilles tendon, cow extensor tendon and calf extensor tendon. It was unexpectedly found that the yield of acid-extractable collagen from the calf common digital extensor tendon is about 4 times greater than from the calf achilles tendon and about 2 times greater than from the cow extensor tendon. This increased yield of acid extracted collagen from the common digital extensor tendon, together with its easy accessibility, ease of dissection and relatively low cost, make this tendon a preferred source for the production of collagen. It was also unexpectably found that tissue equivalent produced from collagen extracted from the calf common digital extensor tendon had a much greater tensile strength than tissue equivalents produced from other commercial sources of acid-extractable collagen (see Example 4 below). Comparative yields of acid-extractable collagen from various sources using the acid extraction procedure described hereinafter are illustrated in Table I below.

TABLE I

| COMPARATIVE YIELDS | |
|---|---|
| Collagen Source | Acid soluble collagen (% wet weight) |
| cow tail tendon | 1.0 |

TABLE I-continued
COMPARATIVE YIELDS

| Collagen Source | Acid soluble collagen (% wet weight) |
|---|---|
| calf skin | 2.3 |
| cow Achilles tendon | 0.2 |
| calf Achilles tendon | 1.3 |
| cow extensor tendon | 2.7 |
| calf extensor tendon | 5.1 |

In general, methods of preparing collagen in accordance with the present invention comprise the steps of:

(a) washing finely-divided tendon in a sodium chloride/sodium phosphate buffer;

(b) extracting collagen from the washed tendon with acetic acid and a gentle mechanical action;

(c) precipitating the acid-extracted collagen obtained in step (b) with sodium chloride; and (d) recovering the precipitated collagen.

In one preferred embodiment of the present invention, recovery of the precipitated collagen is accomplished by filtration. In another preferred embodiment of the present invention, precipitation of the acid-extracted and recovery of the precipitated collagen by filtration is accompanied by aeration. In yet another preferred method, the aerated precipitate floats to the surface, most of the liquid is suctioned off and the remaining liquid and precipitate is centrifuged.

When the intended use of the collagen is for an application such as the production of tissue equivalents, the methods of the present invention are carried out under sterile conditions.

It is preferred, in carrying out the methods of the present invention by extraction from bovine tendon, that the tendon sheath be removed. As shown in Table II below, it has been found that removal of the tendon sheath reduces collagen aggregates and decreases the level of non-collagenous contaminants which are observed after production of a contracted living tissue equivalent and subsequent fixing and staining of the lattice. Decreased levels of non collagenous contaminant was shown by the ratio of hydroxyproline/280 nm absorbance.

TABLE II
EFFECT OF SHEATH REMOVAL

| | hydroxyproline/280 nm |
|---|---|
| with sheath | 4.69 |
| without sheath | 7.70 |

After removal of the tendon sheath, the tendon is finely divided, for example, by grinding or mincing. Typically, the finely divided tendon is washed to remove non-collagenous contaminants. Often such washing steps reduce the yield of collagen. It was unexpectedly found that washing the finely divided tendon in phosphate buffered saline (PBS) at a pH of about 6.5 to 8.5 increased the amount of non-collagenous contaminant removed without reduction in yield of collagen. Although a 0.05M NaCl: 2.2 mM phosphate buffer pH 7.4 at 1:3 PBS solution is preferred for the wash step, a range of PBS dilutions from about 1:3 to about 1:1 are useful in the practice of the present invention. The effect of various wash compositions on yield is shown Table III below.

TABLE III
EFFECT OF WASH COMPOSITIONS

| wash | mg non-collagenous protein per g wet tendon removed in the wash | yield of collagen (% wet weight) |
|---|---|---|
| water | 7.7 | 5.04 |
| PBS | 21.7 | 1.68 |
| 1:1 PBS | 16.4 | 3.72 |
| 1:3 PBS | 13.5 | 5.46 |

Extraction of collagen with acid is accompanied by gentle mechanical action in order to reduce the amount of collagen aggregates in the solution. Acids which may be used in extracting collagen in accordance with the present invention include weak acids such as acetic, citric, and formic acid, acetic acid being a preferred extraction agent. The concentration of acid used in the extraction will vary depending upon a number of factors, including the collagen source and acid selected, but is typically from about 0.25 to 2.0M.

In the practice of the present invention, the extracted collagen is recovered by precipitation. Various methods for precipitating extracted collagen are known to those skilled in the art. In a preferred embodiment of the present invention, the acid extracted collagen is precipitated with sodium chloride, typically, at a concentration of from about 0.6M to about 1.8M.

In accordance with the methods of the present invention, precipitated collagen is then recovered, typically by centrifigation. However, in one preferred embodiment of the present invention, the collagen is precipitated and filtered with aeration by a sterile gas, a preferred gas being nitrogen. Aeration makes filtration possible by making the precipitate float, thus, maintaining the filter unclogged for a long enough period to make filtration practical. Filtration offers advantages because it is faster than centrifugation and the resulting precipitate is easier to redissolve.

The properties of typical collagen composition prepared from bovine common digital extensor tendon in accordance with the present invention are illustrated below in Table IV.

TABLE IV
PROPERTIES

| | |
|---|---|
| Collagen Source: | Bovine common digital extensor tendon |
| Viscosity: | 25-60 cSt/s |
| Protein Composition: | 90-99% Type I Collagen as shown by Western blots and CNBr peptide maps. |
| amino acid compositions | residues/1000 |
| Asp | 40-62 |
| Glu | 68-92 |
| Hyp | 83-100 |
| Ser | 33-37 |
| Gly | 280-330 |
| His | 2-5 |
| Arg | 46-61 |
| Thr | 4-38 |
| Ala | 103-121 |
| Pro | 87-128 |
| Tyr | 3-15 |
| Val | 23-35 |
| Met | 8-16 |
| Cys | 0-8 |
| Ile | 1-26 |
| Leu | 24-42 |
| Hyl | 13-20 |
| Phe | 5-2 |

TABLE IV-continued

| PROPERTIES | |
|---|---|
| Collagen Source: | Bovine common digital extensor tendon |
| Viscosity: | 25–60 cSt/s |
| Protein Composition: | 90–99% Type I Collagen as shown by Western blots and CNBr peptide maps. |
| amino acid compositions | residues/1000 |
| Lys | 23–42 |

Tissue equivalents produced from collagen compositions extracted from the calf common digitial extensor tendon were found to have unexpectedly high burst strengths, typically about 200 mm/Hg. A comparison of the burst strengths of tissue equivalents made from various collagen compositions is set forth in Example 4 below.

Thus, we have described a novel source of collagen compositions, providing unexpectedly high yields of extractable collagen; new methods of preparing collagen compositions; and tissue equivalents having improved strength.

This invention will be further understood with reference to the following examples, which are purely exemplary in nature and are not meant to be utilized to limit the scope of the invention.

Sterile procedures are used in the following examples unless otherwise noted. Unless otherwise noted, the 1:3 v/v phosphate buffered saline (PBS) used contained 0.05M sodium chloride: 2.2 mm sodium phosphate pH 7.4.

EXAMPLE 1

Production of Frozen Bovine Tendons

1. Thaw and wash hooves.
2. The common digital extensor tendon was dissected out in two stages.
 (a) Two lateral incisions were made and the dorsal flap of skin was peeled back to expose the common digital extensor tendon (front tendon).
 (b) The tendon was cut away from the surrounding tissue and sheath.
3. The tendons were soaked briefly in water and then stored in a −70° C. freezer until used.

EXAMPLE 2

Preparation of Frozen, Ground, Bovine Tendons

1. Frozen bovine tendons prepared in accordance with Example 1 were held at 2°–8° C. until at least partially or completely thawed.
2. The tendons were simultaneously ground with approximately equal weight of sterile ice.
3. The ground tendon was centrifuged at 20000G for 15 minutes.
4. The ground tendon was stored in −80° C. freezer until used.

EXAMPLE 3

Preparation of Sterile Bovine Collagen 1. 150 grams of frozen, ground bovine tendons prepared in accordance with Example 2 were thawed and added to 15.0L of cold (2°–8° C.) sterile PBS:water (1:2 v/v) in a BELCO top stirring reaction vessel.
2. The BELCO (MODEL 7764-00110) was run at a setting of 10 for 2 hours at 2°–8° C.
3. The buffer was aspirated and the washing step was repeated 5 more times.
4. 15 L of sterile 2.8% acetic acid (2°–8° C.) was added to the vessel and the motor run at setting 5 for 72 hours at 2°–8° C.
5. The suspension was decanted and centrifuged at 25,000G and 4° C. for 30 minutes in a Beckman Model No. J221.
6. The top-most layer was removed and placed into another 15 L BELCO top stirrer vessel.
7. 3 L of cold, sterile 3.6 m sodium chloride solution was then added to the Belco flask and mixed, with simultaneous aeration with sterile nitrogen at 2°–8° C. for 1 hour.
8. The precipitate from step 7 was collected by filtration using an Amicon 2000 filter unit and its support disk.
9. 2 L of cold, sterile 2.8% acetic acid was immediately added to the filter unit and stirred at maximum setting for 2°–8° C. for 30 min. The solution was transferred to a 15 L BELCO vessel.
10. If any precipitate remained, Step 9 was repeated until all precipitate is dissolved.
11. Steps 7–10 were repeated.
12. The volume of solution in the Belco vessel was brought to 5 L by the addition of 2.8% acetic acid. Glacial acetic acid was added to a final concentration of 1M and mixed at speed 5 for 72 hours at 2°–8° C.
13. The contents of the BELCO flask transferred to dialysis tubing and dialyzed against 100 L of cold (2°–8° C.), 0.05% acetic acid for 24 hours.
14. After 20–24 hours, the acetic acid was replaced.
15. Step 14 was repeated.
16. The contents of the dialysis tube was transferred to sterile, screw cap bottles and stored at 2°–8° C. until use.

EXAMPLE 4

Burst Strength of Living Skin Tissue Equivalents

Dermal equivalents formed using different collagen preparations, as identified below, were cast in 60 mm petri dishes in accordance with procedures disclosed in the Patents. In general, such tissue equivalents are produced by a method comprising:

(a) Combining a collagen solution with a contractile agent under conditions to form a gel mixture having the contractile agent dispersed within the gel mixture; and (b) Maintaining the gel mixture prepared in step (a) under conditions which permit contraction of the gel mixture to form a tissue equivalent.

The casting mixture contained 0.49 ml of 10× DMEM, 0.54 ml of fetal bovine serum, 0.05 ml of 200 mM glutamine, 6 ul of 50 mg/ml Gentamicin sulfate, 0.15 ml of 71.2 mg/ml sodium bicarbonate, 4 ml of 1 mg/ml collagen, and 0.6 ml of a suspension of $2.5 \times 10^5$ human dermal fibroblasts in DMEM supplemented with 10% serum.

The dermal equivalents described above were incubated at 36° C. and 10% $CO_2$ for 7 days and hydrodynamic burst strength determined on a 7 mm diameter sample. The results are set forth below:

| Collagen Source | Burst Strength in mm/Hg |
|---|---|
| Acid extracted tendon collagen prepared according to Examples 1–3 above. | About 150 to 250 |

| Collagen Source | Burst Strength in mm/Hg |
| --- | --- |
| Pepsin extracted Common digital extensor tendon. | 6-10 |
| Acid extracted bovine dermal collagen produced by Bioetica. | 18-30 |
| Pepsin extracted porcine dermal collagen produced by Pentapharm. | 5-10 |
| Acid extracted rat tail tendon collagen prepared in accordance with the method of Examples 1-3 above. | 60-90 |

It is understood that the examples and embodiments described herein are for illustrative purposes only and that various modifications or changes, in light thereof, that will be suggested to persons skilled in the art are to be included in the spirit and purview of this application and the scope of the approved claims.

What is claimed is:

1. A method of preparing collagen from tendon comprising:
   (a) washing finely divided common digital extensor tendon from which the sheath has been removed in phosphate buffered saline at a pH of about 6.5 to 8.5;
   (b) extracting collagen from the tendon obtained in step (a) with a weak acid and gentle mechanical action;
   (c) precipitating the acid-extracted collagen obtained in step (b); and
   (d) recovering the precipitated collagen.

2. The method of claim 1, wherein the tendon is calf common digital extensor tendon.

3. The method of claim 1, wherein the phosphate buffered saline comprises 0.05M sodium chloride: 2.2 mM sodium phosphate buffer at a ratio of about 1:3 to 1:1.

4. The method of claim 3, wherein the ratio is about 1:3.

5. The method of claim 1, wherein the acid is acetic, citric or formic acid.

6. The method of claim 5, wherein the acid is acetic acid.

7. The method of claim 1, wherein the acid extracted collagen is precipitated with sodium chloride.

8. The method of claim 7, wherein the sodium chloride is at about 0.6 to 1.8M.

9. The method of claim 1, wherein steps (c) and (d) are accomplished by simultaneous precipitation and aeration, followed by pressure filtration of the precipitated collagen.

10. The method of claim 1, wherein the precipitated collagen is recovered by filtration with aeration.

11. The method of claim 1, wherein the yield of collagen is greater than about 4% of the wet weight of the finely divided tendon.

12. A Type I collagen composition comprising collagen extracted from common digital extensor tendon in accordance with the method of claim 1.

13. The collagen composition of claim 12, wherein the tendon is calf common digital extensor tendon.

14. A collagen composition in accordance with claim 12, wherein the collagen extracted is at least about 3% to 6% of the wet weight of the tendon.

15. A tissue equivalent comprising Type I collagen extracted from common digital extensor tendon in accordance with the method of claim 1.

16. The tissue equivalent of claim 15, wherein the tendon is calf common digital extensor tendon.

17. The tissue equivalent of claims 15, wherein the burst strength is at least 200 mm Hg.

18. The tissue equivalent of claim 15, wherein the burst strength is about 110 to 150 mm Hg.

* * * * *